United States Patent [19]

Curran

[11] 3,960,876

[45] June 1, 1976

[54] CERTAIN 1-CARBOTHIOAMIDES OF 1,8-NAPHTHYRIDINES, PYRROLO(2,3-b)PYRIDINES AND PYRIDO(2,3-b)AZEPINES

[75] Inventor: Adrian Charles Ward Curran, Newcastle-upon-Tyne, England

[73] Assignee: John Wyeth & Brother, Ltd., Maidenhead, England

[22] Filed: Feb. 28, 1975

[21] Appl. No.: 553,964

[30] Foreign Application Priority Data

Mar. 5, 1974     United Kingdom................. 9764/74
July 12, 1974    United Kingdom............... 30935/74

[52] U.S. Cl........................... 260/294.8 C; 424/263

[51] Int. Cl.²....................................... C07D 213/83
[58] Field of Search.............. 260/294.8 C; 424/263

[56] References Cited

UNITED STATES PATENTS 3,149,104    9/1964    Lesher et al.................... 260/295 N

*Primary Examiner*—Alan L. Rotman

[57] ABSTRACT

The invention relates to thioureas which are derivatives of organic nitrogen compounds containing a pyridine ring to which is fused a saturated nitrogen containing ring which carries on its nitrogen atom a thioamide or substituted thioamide group. The compounds are anti-ulcer agents or intermediates therefor.

9 Claims, No Drawings

CERTAIN 1-CARBOTHIOAMIDES OF 1,8-NAPHTHYRIDINES, PYRROLO(2,3-B)PYRIDINES AND PYRIDO(2,3-B)AZEPINES

The invention relates to novel organic nitrogen compounds, to processes for preparing them and to pharmaceutical compositions containing them.

According to the invention there is provided compounds of formula (I)

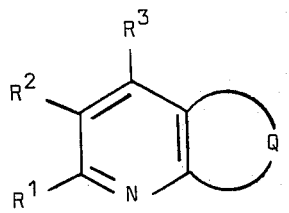

(I)

and pharmaceutically acceptable acid addition salts thereof wherein $R^1$, $R^2$ and $R^3$ are the same or different and represent a hydrogen atom or a lower alkyl, phenyl lower alkyl or, phenyl radical, any of which radicals may be substituted by lower alkyl, lower alkoxy, halogen, nitro or trifluoromethyl, Q is the group

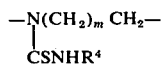

wherein $m$ is 1, 2 or 3, and the group Q may be substituted by one or more lower alkyl, phenyl lower alkyl or phenyl radicals any of which radicals may be substituted by alkyl, alkoxy, halogen, nitro or trifluoromethyl and $R^4$ is hydrogen, alkyl of 1–3 carbon atoms which may be substituted by diloweralkylamino; lower alkanoyl or aroyl.

When any of $R^1$, $R^2$ or $R^3$ is a lower alkyl radical or there is a lower alkyl substituent in ring Q then this may be a straight or branched chain, having from 1 to 6 carbon atoms, e.g. methyl, ethyl, n-, and iso-propyl and n, s- and t-butyl. The term alkyl radical is also intended to embrace cyclic alkyl radicals e.g. cyclobutyl, cyclopentyl and cyclohexyl. When any of $R^1$, $R^2$ and $R^3$ is a phenyl lower alkyl radical or there is a phenyl lower alkyl substituent in ring Q the lower alkyl portion may be as discussed immediately above for a lower alkyl radical.

When any of $R^1$, $R^2$ or $R^3$ is a phenyl radical, or ring Q has a phenyl substituent this is preferably phenyl or a substituted phenyl radical (substituted by lower alkyl, lower alkoxy, halogen, nitro or trifluoromethyl).

The term "lower alkoxy" as used in this specification means alkoxy radicals having from 1 to 6 carbon atoms e.g. methoxy, ethoxy, propoxy, butoxy, pentoxy and hexoxy.

Particularly preferred compounds are those in which at least one of $R^1$, $R^2$ and $R^3$ is methyl and the others are hydrogen. Also preferred are compounds wherein $m$ is 1 or 3.

The group $R^4$ may be methyl, ethyl or n-propyl. Preferably $R^4$ is methyl.

Examples of aroyl groups are benzoyl and substituted benzoyl e.g. halobenzoyl, such as chlorobenzoyl. The lower alkanoyl group is one having from 2 to 7 carbon atoms e.g. acetyl, propionyl, butyryl, pentanoyl and hexanoyl.

When the nitrogen atoms of the group Q is adjacent to the nitrogen atom of the pyridine ring in the compounds of formula I the compounds are aza compounds of formula Ia

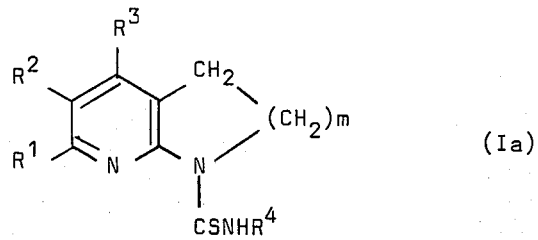

(Ia)

wherein $R^1$, $R^2$, $R^3$, $R^4$ and $m$ are as defined above in connection with formula I and the saturated ring may be substituted as discussed in connection with formula I.

When the nitrogen atom of the group Q is joined to the other position of the pyridine ring the compounds have the formula Ib

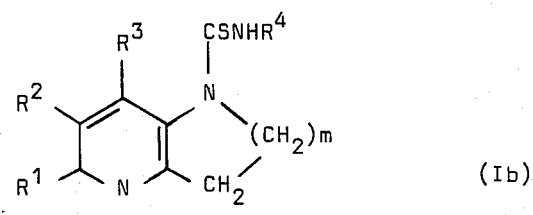

(Ib)

wherein $R^1$, $R^2$, $R^3$, $R^4$ and $m$ are as defined in connection with formula I and the unsaturated ring may be substituted as discussed in connection with formula I.

Compounds of formula I wherein $R^4$ is hydrogen or alkyl of 1–3 carbon atoms which may be substituted by dialkylamino are anti-ulcer agents, which are active in one or more of the following pharmacological tests namely anti-ulcer, anti-secretory or gastric anti-histamine activity. The other compounds are intermediates which may be used in the preparation of the active compounds.

It has been found that compounds of formula Ia wherein $m$ is 3 and $R^4$ is H or methyl are more active as anti-secretory agents than corresponding compounds wherein m is 1 or 2.

Accordingly in a preferred aspect the present invention provides compounds of formula II

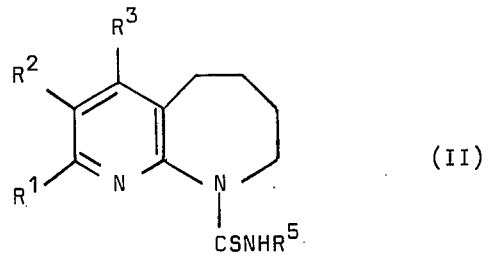

(II)

and the acid addition salts thereof wherein $R^5$ is hydrogen or methyl and the groups $R^1$, $R^2$ and $R^3$ are as defined above in connection with formula Ia.

Preferably $R^1$, $R^2$ and $R^3$ are selected from hydrogen and methyl.

The invention includes processes for preparing the compounds of formula I.

A process for preparing compounds of formula I wherein $R^4$ is alkyl of 1–3 carbon atoms which may be substituted by dialkylamino; lower alkanoyl or aroyl comprises reacting a compound of formula I wherein Q is —NH(CH$_2$)$_m$CH$_2$— and $R^1$, $R^2$, $R^3$ and $m$ are as defined in connection with formula I with an isothiocyanate of formula $R^4$NCS wherein $R^4$ is defined immediately above.

Compounds of formula I, wherein $R^4$ is hydrogen may be prepared by hydrolysing a compound of formula I wherein $R^4$ is lower alkanoyl or aroyl.

The hydrolysis may be carried out by treatment with a suitable base e.g. an alkali or alkaline earth metal hydroxide. Conveniently sodium or potassium hydroxide may be used.

The compounds of formula I can form acid addition salts with inorganic acids e.g. hydrochloric, hydrobromic, sulphuric or nitric acids, or organic acids e.g. citric, fumaric, maleic or tartaric acids. These acid addition salts are included in the invention.

As stated above the active compounds of formula I, wherein $R^4$ is hydrogen, or alkyl of 1–3 carbon atoms, which may be substituted by dialkylamino; are antiulcer agents which display activity in tests for one or more of the following: anti-ulcer, anti-secretory or gastric anti-histamine activity. Anti-ulcer activity is determined by the method of Brodie and Hanson, J. Applied Physiology, 15, 291, 1960. Anti-secretory activity and gastric antihistamine activity are determined by the method of H. Shay, D. Sun and H. Greenstein, Gastroenterology 1954, 26, 906-13.

The invention includes a pharmaceutical composition comprising an active compound of formula I (as defined immediately above) including non-toxic salts thereof, and a pharmaceutically acceptable carrier.

For the pharmaceutical carrier any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be capsule, cachet or tablet itself, or it can be the appropriate number of any of these in packaged form. The quantity of active ingredient in a unit dose of composition may be carried or adjusted from 5 mg. or less to 500 or more, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients e.g. aluminium hydroxide, magnesium hydroxide or bismuth carbonate, aluminium glycinate, calcium carbonate magnesium trisilicate, sodium bicarbonate or the alumina gel described in British Pat. specification No. 1,284,394.

The invention is illustrated by the following Examples. Temperatures are in °C.

EXAMPLE I

7-Aza-1-(N-methylthiocarboxamido)-indoline

7-Azaindoline was prepared from 7-azaindole by the procedure described in J.A.C.S. 1957, 79, 2573 and was isolated as a colourless oil b.p. 114°/10 mm. which crystallised as colourless needles m.p. 83°.

A solution of 7-azaindoline (1.32 g., 0.011 mol.) in acetonitrile (15 ml.) was treated with methylisothiocyanate (0.81 g., 0.011 mol.) and the mixture heated at reflux with stirring for 3 hours. The solvent was removed and the residue crystallised from absolute ethanol to give the title compound as pale yellow needles (0.85 g.) m.p. 109°C. (Found: C, 56.2; H, 5.9; N, 21.7%. C$_9$H$_{11}$N$_3$S requires: C, 55.9; H, 5.7; N, 21.7%).

The product displays antisecretory activity and anti-ulcer activity.

EXAMPLE 2

7-Aza-1-(N-benzoylthiocarboxamido)-indoline

The title compound was prepared from 7-azaindoline (1.5 g.) and N-benzoylisothiocyanate (2.0 g.) by the procedure described in Example 1 and was isolated as colourless needles (1.66 g.) from acetonitrile m.p. 195°. (Found: C, 63.6; H, 4.7; N, 15.0. C$_{15}$H$_{13}$N$_3$OS requires: C, 63.6; H, 4.6; N, 14.8%).

The product is an intermediate for the compound of the next example.

EXAMPLE 3

7-Azaindoline-1-thiocarboxamide

7-Aza-1-(N-benzoylthiocarboxamido)-indoline (1 g.) was treated with 10% sodium hydroxide (10 ml.) and the mixture heated at reflux with stirring for 10 minutes. The cooled reaction mixture was filtered and the solid washed with water (3 × 10 ml.) and dried to give the title compound as a white powder (0.5 g.) m.p. 173°. (Found: C, 53.5; H, 5.1; N, 23.5. $C_8H_9N_3S$ requires: C, 53.6; H, 5.1; N, 23.4%).

The product displays anti-secretory activity.

EXAMPLE 4

1,2,3,4-Tetrahydro-1-(N-methylthiocarboxamido)-1,5-naphthyridine 1,5-Naphthyridine was prepared from 3-aminopyridine according to the method descried in J. Org. Chem., 1963, 1757 and was isolated as colourless needles from n-hexane m.p. 69°C (lit. 74°). 1,5-Naphthyridine 2.6 g.) was hydrogenated in 95% ethanol over $PtO_2$ catalyst under atmospheric conditions to give 1,2,3,4-tetrahydro-1,5-naphthyridine as colourless needles (2.51 g.).

1,2,3,4-Tetrahydro-1,5-naphthyridine (1.34 g., 0.01 mol.) was dissolved in acetonitrile (12 ml.) and treated with methylisothiocyanate (0.73 g., 0.01 mol.) and the mixture heated at reflux with stirring for 3 hours. The solvent was removed in vacuo and the residue recrystallised from isopropanol to give the title compound as colourless needles (0.9 g.) m.p. 120°C. (Found: C, 58.4; H, 6.6; N, 20.3. $C_{10}H_{13}N_3S$ requires: C, 57.9; H, 6.3; N, 20.3%).

EXAMPLE 5

1,2,3,4-Tetrahydro-1-(N-methylthiocarboxamido)-1,8-naphthyridine 1,2,3,4-Tetrahydro-1,8-naphthyridine was prepared from 3-(3-pyridyl)propan-1-ol according to the method of Hawes et al (J. Het. Chem. 1973, 10, 39) and was isolated as colourless needles Bpt. 88°/0.15 mmHg. The title compound was prepared from 1,2,3,4-tetrahydro-1,8-naphthyridine and methylisothiocyanate by the method described in Example 1 and was isolated as colourless needles m.p. 78°C. (Found: C, 58.4; H, 6.5; N, 20.3. $C_{10}H_{13}N_3S$ requires: C, 57.9; H, 6.3; N, 20.3%).

EXAMPLE 6

6,7,8,9-Tetrahydro-9-(N-methylthiocarboxamido)-5H-pyrido[2,3-b]-azepine 6,7,8,9-Tetrahydro-5H-pyrido[2,3-b]azepine (1.48 g., 0.01 mol.), prepared from 4-(3'-pyridyl)-butylamine according to the method of Hawes and Davis (J. Het. Chem. 1973, 10, 39), was dissolved in acetonitrile (15 ml.) and treated with methyl isothiocyanate (0.75 g., 0.01 mol.). The solution was heated at reflux for 3 hours, cooled and the volatiles removed in vacuo. The residual oil was dissolved in ether (25 ml.) and treated with an excess of ethereal hydrogen chloride. The resultant solid was removed and recrystallised from isopropanol to give the hydrochloride of the title compound as colourless needles (0.9 g.) m.p. 192°C. (Found: C, 51.0; H, 6.5; N, 16.2. $C_{11}H_{15}N_3S.HCl$ requires: C, 51.2; H, 6.3; N, 16.3%). The product displayed marked anti-secretory activity at 10 m.p.k.

EXAMPLE 7

6,7,8,9-Tetrahydro-5H-pyrido[2,3-b]azepine-9-thiocarboxamide 6,7,8,9-Tetrahydro-5H-pyrido[2,3-b]azepine (2 g., 0.013 mol.) in acetonitrile (20 ml.) was treated with a solution of benzoylisothiocyanate (2.2 g., 0.013 mol.) in acetonitrile (10 ml.) and the mixture heated at reflux for 1 hour. The reaction mixture was cooled and filtered to give 6,7,8,9-tetrahydro-9-(N-benzoylthiocarboxamido)-5H-pyrido[2,3-b]azepine as colourless needles (3 g.) m.p. 154°C. (Found: C, 65.4; H, 5.8; N, 13.7 $C_{17}H_{17}N_3OS$ requires: C, 65.6; H, 5.5; N, 13.5%).

The benzoyl thiourea (2.7 g.) was treated with 10% aqueous sodium hydroxide solution (15 ml.) and the mixture heated at reflux for 1.5 hours. The cooled reaction mixture was filtered and the solid recrystallised from isopropanol to give the title compound as colourless needles (0.4 g.) m.p. 121°C. (Found: C, 57.7; H, 6.6; N, 20.3; $C_{10}H_{13}N_3S$ requires: C, 57.9; H, 6.3; N, 20.3%).

The product displayed marked anti-secretory activity.

EXAMPLE 8

7 - Aza - 2 - methyl - 1 - (N - methylthiocarboxamido) - indoline

The title compound is prepared from 2-methyl-7-azaindoline and methyl isothiocyanate by the method described in Example 1.

EXAMPLE 9

7-Aza-4-methyl-1-(N-methylthiocarboxamido)-indoline

The title compound is prepared from 4-methyl-7-azaindoline and methyl isothiocyanate by the method described in Example 1.

EXAMPLE 10

1,2,3,4-Tetrahydro-5,7-dimethyl-1-(N-methylthiocarboxamido) 1,8-naphthyridine The title compound is prepared from 1,2,3,4-tetrahydro-5,7-dimethyl-1,8-naphthyridine and methyl isothiocyanate by the method described in Example 1.

EXAMPLE 11

1,2,3,4-Tetrahydro-1-(N-methylthiocarboxamido) 3-phenyl-1,8-naphthyridine

The title compound is prepared from 1,2,3,4-tetrahydro-3-phenyl-1,8-naphthyridine and methyl isothiocyanate by the method described in Example 1.

EXAMPLE 12

7-Aza-1-(N-ethylthiocarboxamido)-indoline

The title compound is prepared by treating 7-azaindoline with ethyl isothiocyanate by the method described in Example 1.

EXAMPLE 13

7-Aza-1-(N-n-propylthiocarboxamido)-indoline

The title compound is prepared by treating 7-azaindoline with n-propyl isothiocyanate according to the method described in Example 1.

EXAMPLE 14

9-(N-ethylthiocarboxamido)-6,7,8,9-tetrahydro-5H-pyrido[2,3-b]azepine

The title compound is prepared by treating 6,7,8,9-tetrahydro-5H-pyrido[2,3-b] azepine with ethyl isothiocyanate and converted to the hydrochloride according to the procedure described in Example 6.

EXAMPLE 15

7-Aza-1-[N-(2-diethylaminoethyl)thiocarboxamido]-indoline

The title compound is prepared from 7-azaindoline and diethylaminoethyl isothiocyanate by the method described in Example 1.

EXAMPLE 16

9-[N-(2-Diethylaminoethyl)thiocarboxamido]-6,7,8,9-tetrahydro-5H-pyrido[2,3-b]azepine The title compound is prepared from 6,7,8,9-tetrahydro-5H-pyrido[2,3-b]azepine and diethylaminoethyl isothiocyanate and then isolated as a dihydrochloride using the general procedure of Example 6.

EXAMPLE 17

1-(N-Acetylthiocarboxamido)-7-azaindoline

Following the procedure of Example 2 7-azaindoline is treated with N-acetyl isothiocyanate to give the title compound, which may be hydrolysed in the manner described in Example 3 to give 7-azaindoline-1-thiocarboxamide.

EXAMPLE 18

1-(N-Ethylthiocarboxamido)-1,2,3,4-tetrahydro-1,5-naphthyridine 1,2,3,4-Tetrahydro-1,5-naphthyridine is treated with ethyl isothiocyanate according to the procedure of Example 4 to obtain the title compound.

EXAMPLE 19

1-[N-(2-Diethylaminoethyl)thiocarboxamido]-1,2,3,4-tetrahydro-1,5-naphthyridine The title compound is prepared from 1,2,3,4-tetrahydro-1,5-naphthyridine and diethylaminoethyl isothiocyanate following the procedure of Example 4.

EXAMPLE 20

1-(N-p-Chlorobenzoylthiocarboxamido)-1,2,3,4-tetrahydro-1,5-naphthyridine 1,2,3,4-Tetrahydro-1,5-naphthyridine is treated with p-chlorobenzoyl isothiocyanate according to the method of Example 4 to give the title compound which may be hydrolysed with 10% sodium hydroxide to give 1,2,3,4-tetrahydro-1,5-naphthyridine-1-thiocarboxamide.

I claim:
1. A compound of formula (I)

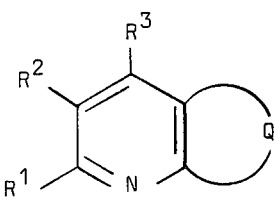

(I)

or a pharmaceutically acceptable acid addition salt thereof wherein $R^1$, $R^2$ and $R^3$ are the same or different and represent a hydrogen atom or a lower alkyl, phenyl lower alkyl or, phenyl radical, any of which radicals may be substituted by lower alkyl, lower alkoxy, halogen, nitro or trifluoromethyl, Q is the group $$-\underset{\underset{CSNHR^4}{|}}{N}(CH_2)_m CH_2-$$

wherein N of said group is directly attached to the alpha carbon of pyridine ring, $m$ is 1, 2 or 3, and the group Q may be substituted by lower alkyl, phenyl lower alkyl, or phenyl radicals any of which radicals may be substituted by lower alkyl, lower alkoxy, halogen, nitro or trifluoromethyl and $R^4$ is hydrogen or alkyl of 1–3 carbon atoms.

2. A compound as claimed in claim 1, wherein $R^1$, $R^2$ and $R^3$ are selected from hydrogen and methyl.

3. A compound as claimed in claim 1, wherein $R^4$ is methyl.

4. A compound as claimed in claim 1, which has formula (Ia)

(Ia)

wherein $R^1$, $R^2$, $R^3$, $R^4$ and m are as defined in claim 1.

5. A compound as claimed in claim 1 which has formula II.

(II)

or a pharmaceutically acceptable acid addition salt thereof wherein $R^1$, $R^2$ and $R^3$ are as defined in claim 1 and $R^5$ is hydrogen or methyl.

6. A compound as claimed in claim 1, which is 6,7,8,9-Tetrahydro-9-(N-methylthiocarboxamido)-5H-pyrido[2,3-b] azepine or a pharmaceutically acceptable acid addition salt thereof.

7. A compound as claimed in claim 1, which is 1,2,3,4-tetrahydro-1-(N-methylthiocarboxamido)-1,8-naphthyridine.

8. A compound as claimed in claim 1 which is 2,3-dihydro-N-methyl-1H-pyrrolo[2,3-b]pyridine-1-carbothioamide.

9. A compound as claimed in claim 1 which is 2,3-dihydro-1H-pyrrolo[2,3-b]pyridine-1-carbothioamide.

* * * * *